(12) United States Patent
Eppes et al.

(10) Patent No.: US 6,488,405 B1
(45) Date of Patent: Dec. 3, 2002

(54) FLIP CHIP DEFECT ANALYSIS USING LIQUID CRYSTAL

(75) Inventors: David Harry Eppes, Austin, TX (US); Michael Richard Bruce, Austin, TX (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 09/520,597

(22) Filed: Mar. 8, 2000

(51) Int. Cl.$^7$ .................... G01R 31/00; G01K 11/00; G01N 25/72

(52) U.S. Cl. ................. 374/5; 374/161; 324/760; 324/765

(58) Field of Search ................. 374/5, 1, 161, 374/121, 137, 112, 162, 15, 4, 6, 7; 324/760, 765

(56) References Cited

U.S. PATENT DOCUMENTS

| | | | | |
|---|---|---|---|---|
| 4,455,741 A | * | 6/1984 | Kolodner | 29/574 |
| 4,481,664 A | * | 11/1984 | Linger et al. | 382/8 |
| 4,632,294 A | * | 12/1986 | Druschel et al. | 228/119 |
| 5,403,649 A | * | 4/1995 | Morgan et al. | 428/209 |
| 5,561,293 A | * | 10/1996 | Peng et al. | 250/307 |
| 5,568,564 A | * | 10/1996 | Ozaki | 382/149 |
| 5,705,821 A | * | 1/1998 | Barton et al. | 250/458.1 |
| 5,900,675 A | * | 5/1999 | Appelt et al. | 257/778 |
| 5,949,064 A | * | 9/1999 | Chow et al. | 250/214 LS |
| 6,033,107 A | * | 3/2000 | Farina et al. | 374/5 |
| 6,072,178 A | * | 6/2000 | Mizuno | 250/310 |
| 6,073,479 A | * | 6/2000 | Shapiro et al. | 73/29.01 |
| 6,075,880 A | * | 6/2000 | Kollhof et al. | 382/141 |
| 6,078,183 A | * | 6/2000 | Cole, Jr. | 324/752 |
| 6,087,722 A | * | 7/2000 | Lee et al. | 257/723 |
| 6,146,014 A | * | 11/2000 | Bruce et al. | 374/161 |
| 6,154,039 A | * | 11/2000 | Wu | 324/752 |
| 6,159,755 A | * | 12/2000 | Khosropour et al. | 438/14 |
| 6,175,665 B1 | * | 1/2001 | Sawada | 382/303 |
| 6,180,226 B1 | * | 1/2001 | McArdle et al. | 428/332 |
| 6,181,153 B1 | * | 1/2001 | Mahanpour | 324/765 |
| 6,183,933 B1 | * | 2/2001 | Ishikawa et al. | 430/256 |
| 6,219,723 B1 | * | 4/2001 | Hetherington et al. | 710/18 |
| 6,281,025 B1 | * | 8/2001 | Ring et al. | 438/10 |
| 6,285,036 B1 | * | 9/2001 | Goruganthu et al. | 250/559.27 |
| 6,292,367 B1 | * | 9/2001 | Sikka et al. | 361/705 |
| 6,297,995 B1 | * | 10/2001 | McConnel et al. | 365/201 |

FOREIGN PATENT DOCUMENTS

EP 0177722 A1 * 4/1986 ........... G01R/31/28

OTHER PUBLICATIONS

D. L. Burgess and O. D. Trapp, *Failure and Yield Analysis Handbook*, Oct. 1992, pp. 7.9–7.16.

D. Burgess, *Electronic Failure Analysis: Seminar Reference, Liquid Crystal Hot Spot Detection*, ASM International, 1998, pp. 143–145.

*Failure Analysis of Integrated Circuits: Tools and Techniques*, Lawrence C. Wagner, Ed., 1999, pp. 70–77.

Khandekar, S and Wills, K.S., *Micro Electronic Failure Analysis: Liquid Crystal Microscopy*, ASM International, 1993, pp. 141–144.

* cited by examiner

Primary Examiner—Diego Gutierrez
Assistant Examiner—Gail Verbitsky

(57) ABSTRACT

Defect analysis of a flip chip die having a back side opposite circuitry at a circuit side and a liquid crystal layer is enhanced using a method and system that makes possible the detection of the defect from the back side of the flip chip. According to an example embodiment of the present invention, a flip chip die having a liquid crystal layer is analyzed by detecting a liquid crystal phase change caused by heat generation at a defect in the die. By detecting the phase change associated with a defect, the defect can be located. The defect detection can be used through the back side of the die, and can be used to detect defects located near intrinsic heat sources that make conventional liquid crystal analysis difficult or even impossible.

36 Claims, 7 Drawing Sheets

FLIP CHIP DEFECT ANALYSIS USING LIQUID CRYSTAL

FIELD OF THE INVENTION

The present invention relates generally to semiconductor devices and their fabrication and, more particularly, to semiconductor devices and their manufacture involving techniques for analyzing and debugging circuitry within an integrated circuit.

BACKGROUND OF THE INVENTION

The semiconductor industry has recently experienced technological advances that have permitted dramatic increases in circuit density and complexity, and equally dramatic decreases in power consumption and package sizes. Present semiconductor technology now permits single-chip microprocessors with many millions of transistors, operating at speeds of hundreds of millions of instructions per second to be packaged in relatively small, air-cooled semiconductor device packages. A by-product of such high-density and high functionality in semiconductor devices has been the demand for increased numbers of external electrical connections to be present on the exterior of the die and on the exterior of the semiconductor packages which receive the die, for connecting the packaged device to external systems, such as a printed circuit board.

To increase the number of pad sites available for a die, to reduce the electrical path to the pad sites, and to address other issues, various chip packaging techniques have been developed. One of these techniques is referred to as controlled collapse chip connection or "flip-chip" packaging. With packaging technology, bonding pads of the die include metal (solder) bumps. Electrical connection to the package is made when the die is "flipped" over and soldered to the package. Each bump connects to a corresponding package inner lead. The resulting packages are low profile and have low electrical resistance and a short electrical path. The output terminals of the package, which are sometimes ball-shaped conductive bump contacts, are typically disposed in a rectangular array. These packages are occasionally referred to as "Ball Grid Array" (BGA) packages. Alternatively, the output terminals of the package may be pins and such packages are commonly known as pin grid array (PGA) packages.

Once the die is attached to such a package the back side portion of the die remains exposed. The transistors and other circuitry are generally formed in a very thin epitaxially-grown silicon layer on a single crystal silicon wafer from which the die is singulated. The side of the die including the epitaxial layer containing the transistors and other circuitry is often referred to as the circuit side or front side of the die. The circuit side of the die is positioned very near the package and opposes the back side of the die. Between the back side and the circuit side of the die is bulk silicon.

The positioning of the circuit side near the package provides many of the advantages of the flip chip. However, in some instances orienting the die with the circuit side face down on a substrate is disadvantageous. Due to this orientation of the die, the transistors and circuitry near the circuit side are not directly accessible for testing, modification or other purposes. Therefore, access to the transistors and circuitry near the circuit side is from the back side of the chip.

As the manufacturing processes for semiconductor devices and integrated circuits increase in difficulty, methods for testing and debugging these devices become increasingly important. Not only is it important to ensure that individual chips are functional, it is also important to ensure that batches of chips perform consistently. In addition, the ability to detect a defective manufacturing process early is helpful for reducing the number of defective devices manufactured. With flip-chip technology, these methods for testing and debugging often require accessing the circuitry through the back side.

One integrated circuit analysis method involves using a liquid crystal material for detecting defects from the front side of an integrated circuit. Liquid crystalline materials have both crystalline solid and liquid characteristics. These characteristics enable their use for thermally analyzing an integrated circuit for defects. When the liquid crystal material is heated, its properties change. One such example change is a color change, and another change is an ordering transition. Available defect analysis methods use the change as an indication of temperature in an integrated circuit, which is useful for detecting defects that cause heat generation. By forming a liquid crystal layer on an integrated circuit, the response of the liquid crystal can be monitored and used to detect hot spots that are an indication of a defect.

One type of liquid crystalline material useful for front side defect analysis is calamatic liquid crystal material having nematic ordering. Calamatic liquid crystals have long, rod-shaped molecules, and those having nematic ordering change under temperature variation from a nematic to an isotropic state. In the nematic state, the liquid crystal alters the polarization of light incident upon it. When the liquid crystal changes to an isotropic state, the polarization of incident light is no longer affected. This change in the effect upon incident light is used to detect a temperature change in the liquid crystal material. The transition temperature at which the change occurs is dependent upon the particular characteristics of the material.

Typical analysis methods that use liquid crystals involve forming a liquid crystal layer on an integrated circuit, heating the circuit with an external source, and observing a change in the state of the liquid crystal. The liquid crystal layer is often formed by adding a solvent, such as pentane, to the liquid crystal material and then applying the material to the surface of an integrated circuit device with an eye-dropper. The solvent evaporates, leaving the liquid crystal material behind. Other liquid crystal application methods include applying liquid crystal with a spreading strip, and applying a drop of liquid crystal on the chip and spinning the chip to spread out the liquid crystal. In addition, a liquid crystal emulsion may be used in place of the liquid crystal mixed with a solvent.

Once the liquid crystal has been applied, the integrated circuit is then heated with an external heater. The heater is used to bring the integrated circuit to within about 0.1 Kelvin of the transition temperature of the liquid crystal material. A microscope is directed at the liquid crystal layer. A suitable microscope includes a polarized light source and a linear polarizer (analyzer) in front of an eyepiece or camera. The integrated circuit is electrically stimulated, thereby heating a defect in the circuit and raising the liquid crystal material over the defect to its transition temperature. The liquid crystal material changes from nematic to isotropic phase, which is evidenced by a dark spot that is detected by the microscope.

It would be beneficial to be able to use the state change properties of liquid crystal for back side analysis of flip chip dies including defect detection. However, it has been discovered that the heat dissipation throughout the backside is prohibitive to accurate use of liquid analysis via the backside, and that certain types of integrated circuits have internal intrinsic heat sources that tend to overwhelm defect-related heat sources. Typical intrinsic heat sources include fast-switching circuits such as phase lock loops (PLL) and crystal oscillators. Such heat sources generate heat during normal operation that is significantly greater than heat generated by surrounding circuitry. These intrinsic heat sources make liquid crystal analysis of defective integrated circuits via the back side even more difficult because the intrinsic heat causes the liquid crystal to change phase.

SUMMARY OF THE INVENTION

Addressing the above and other concerns, the present invention is directed to a method and system for analyzing the back side of a flip chip die involving defect detection using a liquid crystal layer. The defect detection can be used via the back side of the die, and can be used to detect defects located near intrinsic heat sources that make conventional liquid crystal analysis difficult or even impossible. The present invention is exemplified in a number of implementations and applications, some of which are summarized below.

According to an example embodiment of the present invention, a method is adapted for analyzing a flip chip die having a back side opposite circuitry at a circuit side. A flip chip die having a liquid crystal layer formed over a thinned region in the back side is provided for analysis. The thinned region is located in a manner that facilitates sufficient heat transfer to the liquid crystal layer to enable the detection of a defect using a liquid crystal phase change. The die is electrically operated, thereby generating heat in the die circuitry. The heat causes a phase change in the liquid crystal layer, and a defect in the die is detected by detecting a portion of the liquid crystal changing phase. In this manner, liquid crystal analysis can be used for back side analysis.

According to another example embodiment of the present invention, a system is adapted to analyze a flip chip semiconductor die having a back side opposite circuitry at a circuit side and a liquid crystal layer. The system includes an arrangement adapted to provide a flip chip die having the liquid crystal layer formed over a thinned region in the back side. An electrical power supply is adapted to power the die and generate heat in the die circuitry. A testing arrangement is adapted to detect a defect in the die as a portion of the liquid crystal changing phase.

The above summary of the present invention is not intended to describe each illustrated embodiment or every implementation of the present invention. The figures and detailed description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1A:
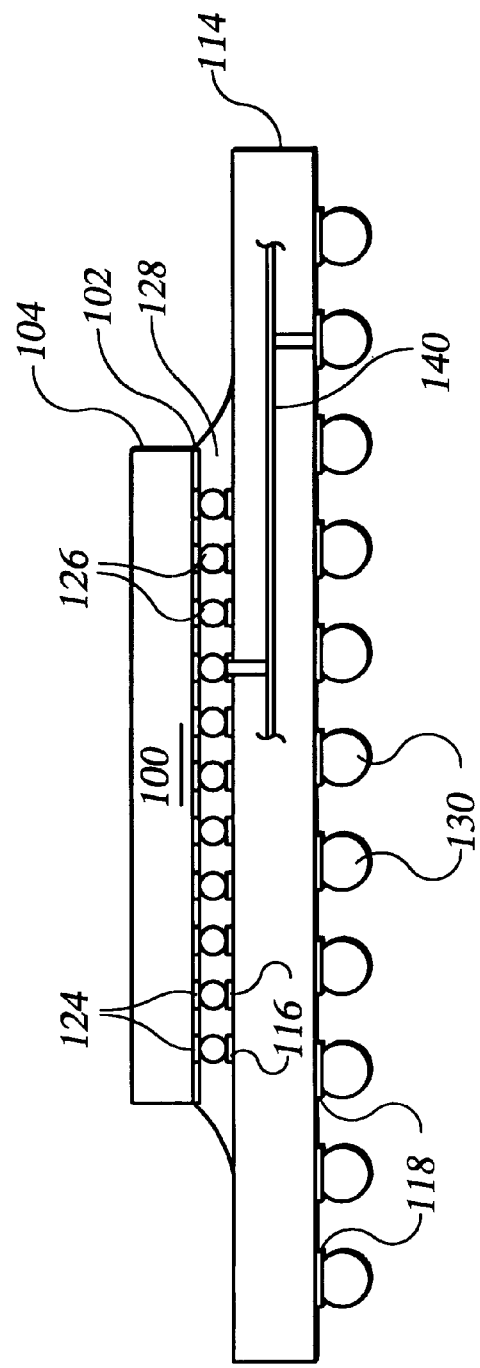
FIG. 1A is a flip chip die bonded to a package substrate, for use in accordance with an example embodiment of the present invention.

While the invention is amenable to various modifications and alternative forms, specifics thereof have been shown by way of example in the drawings and will be described in detail. It should be understood, however, that the intention is not necessarily to limit the invention to the particular embodiments described. On the contrary, the intention is to cover all modifications, equivalents, and alternatives falling within the spirit and scope of the invention as defined by the appended claims.

DETAILED DESCRIPTION

The present invention is believed to be applicable for a variety of different types of semiconductor devices, and the invention has been found to be particularly suited for flip chip dies requiring or benefiting from defect analysis involving the detection of heat that causes liquid crystal to change phase. While the present invention is not necessarily limited to such devices, various aspects of the invention may be appreciated through a discussion of various examples using this context.

According to an example embodiment of the present invention, a flip chip die is analyzed using a phase change of a layer of liquid crystal on a back side of the die to indicate a defect in the die circuitry. The die has circuitry at a circuit side that is opposite the back side, and a liquid crystal layer formed over a thinned region where substrate has been removed from the back side. Herewith, it has been discovered that, by sufficiently removing substrate from the back side of the die, heat transferred from circuitry in the die causes the liquid crystal to change state in a manner that allows the detection of the location of the corresponding heat source. One manner in which the heat can be generated in the die is by powering the defective circuitry within the die. The defective portion of the circuitry generates more heat than would be generated without the defect. In addition, the die can be heated by using an external heat source, using an internal intrinsic heat source (such as a fast-switching circuit), or using a combination thereof. For example internal heat source application, reference may be made to U.S. patent application Ser. No. 09/521,627 entitled "Defect Detection Using Liquid Crystal and Internal Heat Source" and filed concurrently herewith. By removing substrate from the back side, generating heat in the die, and detecting a phase change in the liquid crystal phase, the location of defective circuitry can be determined.

Proper substrate removal from the back side can improve the efficacy of back side liquid crystal analysis. If the back side is not thin enough, the heat may dissipate through the back side in such a manner that a detected liquid crystal phase change may not necessarily provide accurate detection of a defect or other heat source. In addition, an image of the circuitry may not be obtainable if there is too much substrate remaining over the circuitry. If the back side is too thin, damage can result to the die during removal from the package or other operation. In one example embodiment, thinning the back side globally to a thickness slightly greater than about 80 microns was found to be acceptable; typically, the thinned back side should not be thicker than about 100 microns.

It has also been discovered herewith that, when the thinned region is polished appropriately, the liquid crystal adheres well, and an image of the circuitry can be obtained through the thinned region. For example, if the die is highly polished, the liquid crystal may not adhere. If the die is not polished enough, an image may not be obtainable, and deep scratching can cause pooling of the liquid crystal layer during its formation. By polishing the die and limiting any scratches to less than about 3 microns while maintaining adhesion, the liquid crystal layer can be appropriately formed and an image of the circuitry can be acquired through the remaining substrate. The image of the circuitry may, for example, be stored and used for locating the defect by overlaying an image of the liquid crystal phase change on the circuitry image. In another implementation, a circuitry image is obtained from a reference non-defective die having structure that is about identical to the die being tested, and the image of the liquid crystal phase change is overlaid onto the reference image.

In addition to locating a defect as described hereinabove, and according to another example embodiment of the present invention, the thinned back side facilitates locating a defect in the chip even when an intrinsic heat source in the die generates enough heat to overwhelm the heat generated by the defect. The thinned back side permits heat transfer from the defect to the liquid crystal layer in a manner that is sufficient to enable the detection of a defect-generated phase change of the liquid crystal layer before a corresponding phase change due to the intrinsic heat source occurs. The detection may, for example, use the time-lapsed analysis for which reference may be made to U.S. patent application Ser. No. 09/521,260 entitled "Time-lapsed Integrated Circuit Defect Analysis Using Liquid Crystal" and filed concurrently herewith.

FIG. 1 shows a flip chip die 100 bonded to a package 114, for use in connection with an example embodiment of the present invention. The flip chip die 100 has circuitry in a circuit side 102 formed over a back side 104. Solder bumps 126 are formed on the pads 124 that are electrically coupled to the circuitry in the die. The die is flipped over and placed on the package substrate 114 so that the solder bumps contact pads 116 on the substrate. The solder is re-flowed and forms an electrical connection between the pads 124 of the die and the pads 116 of the package. Pads 116 are electrically coupled via interconnects 140 to pads 118 and solder bumps 130 on the package substrate. The bumps 130 can be used to electrically couple the flip chip and package to other electrical components for various semiconductor applications.

Figure 1B:
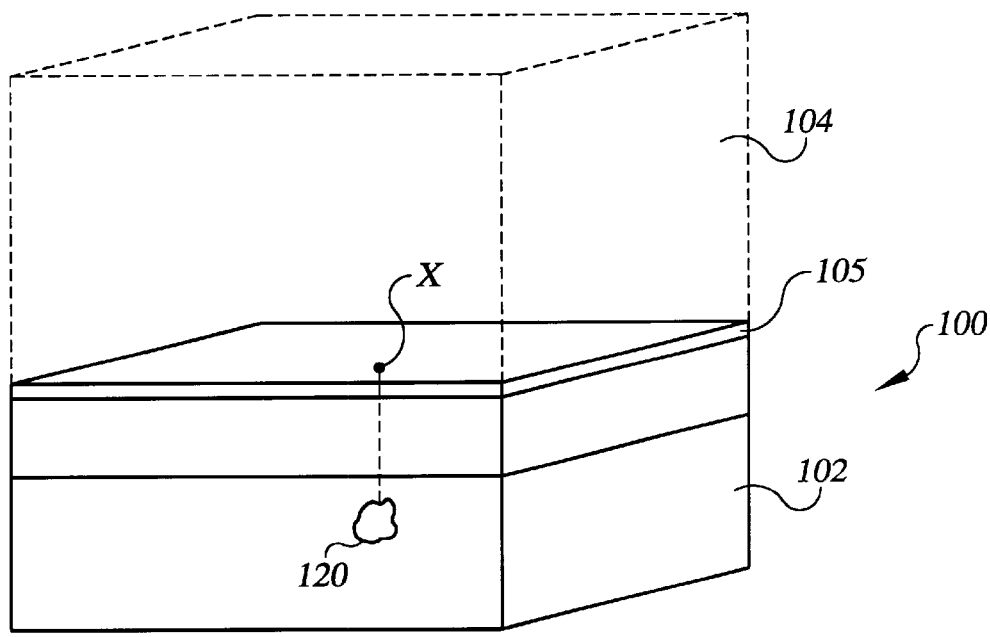
FIG. 1B is the flip chip die of FIG. 1A having substrate removed and a liquid crystal layer, according to an example embodiment of the present invention.
Figure 1C:
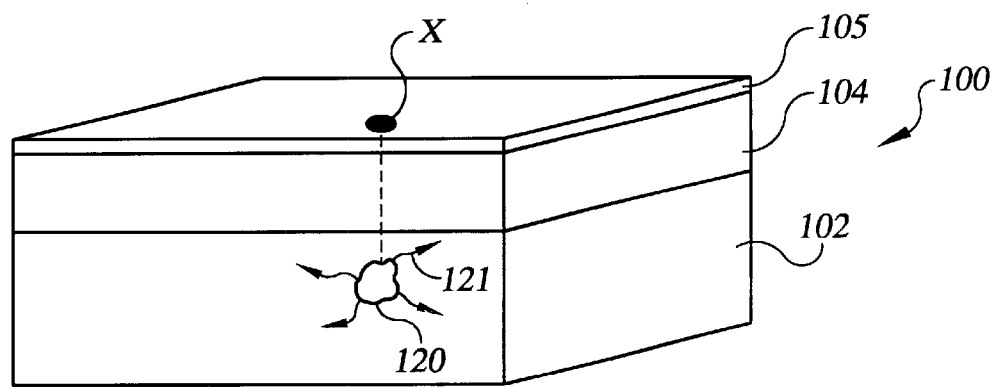
FIGS. 1C–1E is the flip chip die of FIG. 1B undergoing analysis, according to another example embodiment of the present invention.

FIGS. 1B and 1C show a flip chip die 100, such as the flip chip shown in FIG. 1A, undergoing liquid crystal analysis according to another example embodiment of the present invention. A portion (shown dashed) of the backside 104 has been removed to form a thinned region, and a layer of liquid crystal material 105 has been formed over the thinned region. The die has a circuit region 120 in the circuit side 102 and located below region X of the liquid crystal layer 105. The die is powered at FIG. 1C, and the circuit region 120 is electrically heated. The heat 121 generated by the circuit region 120 heats nearby portions of the die. The backside 104 has been sufficiently thinned to facilitate heat transfer from the circuit region 120 in a manner that enables the heating of the liquid crystal layer at region X. As the liquid crystal near region X reaches its transition temperature, it becomes black when viewed. The black portion is used to detect the location of the circuit region 120.

Figure 1D:
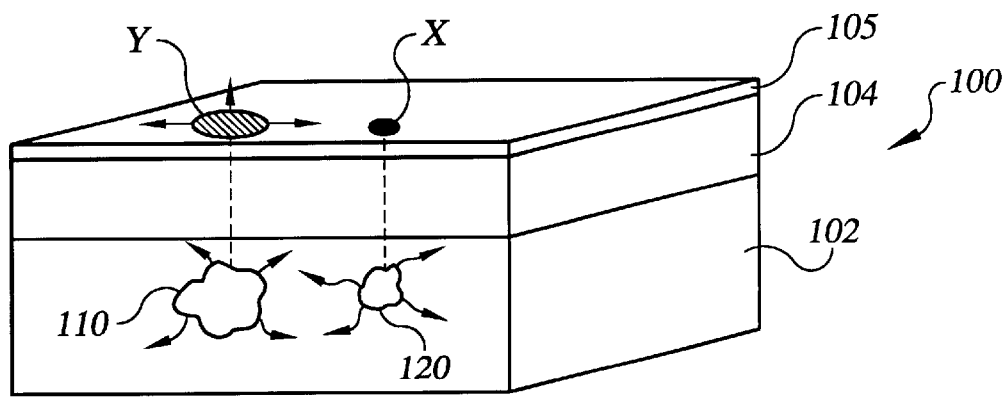
Figure 1E:
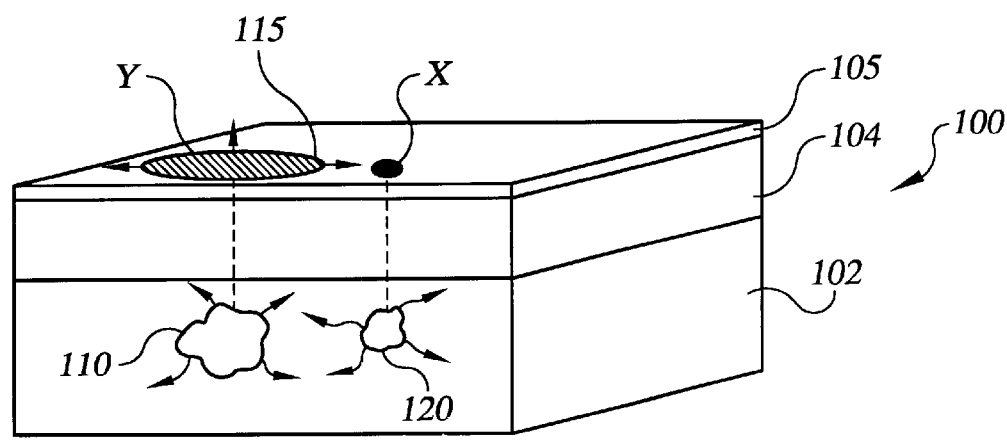

FIGS. 1D and 1E show a flip chip die 100, such as the flip chip shown in FIG. 1A, undergoing liquid crystal analysis according to another example embodiment of the present invention. The die has a first circuit region 110 and a second circuit region 120. A layer of liquid crystal material 105 having a transition temperature is formed over a thinned portion of the back side 104 of the die. Regions Y and X of the liquid crystal layer are located over the first and second circuit regions 110 and 120, respectively.

The die is electrically operated at FIG. 1D, and heat is generated in the die. The heat 111 generated at circuit region 110 is greater than and tends to overwhelm the effect of the heat 121 generated at circuit region 120. As the heat spreads from the circuit regions, the temperature of the surrounding portions of the die increases. The liquid crystal layer is also heated, and when it reaches its transition temperature, it undergoes a phase change viewable as a dark spot that expands radially as the liquid crystal is heated, as shown by way of arrows near region Y.

As shown in FIG. 1E, the circuit regions 110 and 120 continue to generate heat and the leading edge 115 of the liquid crystal that has changed phase near region Y continues to expand and approaches region X. The heat from both of the circuit regions also reaches liquid crystal portion X. Since portion X is being heated by both circuit regions, it changes phase momentarily before the leading edge 115 of the expanding liquid crystal phase change reaches it, shown by a dark spot near region X. Because the back side 104 has been sufficiently thinned, the heat conducted through the thinned portion reaches the portion X in a manner that facilitates the viewing of the phase change due to the circuit region 120.

In another example embodiment, the selected circuit regions are so close that the phase change at region X occurs at such a short time before being engulfed by the leading edge 115 that it ceases to be separately detectable using conventional real-time analysis. In this example, a time-lapsed detector, such as described hereinabove, is adapted to detect the phase change at portion X before it ceases to become separately detectable, enabling liquid crystal analysis of the die 100 using an internal intrinsic heat source.

The liquid crystal layer used in FIGS. 1A–1E may be formed using methods such as those described in the background hereinabove. According to another example embodiment of the present invention, a liquid crystal emulsion, such as BDH K15 liquid crystal, is placed on the die and formed into a substantially even layer over the die using a blast of air. The air blast is selected such that the volume and flow rate of air make possible the even formation of a liquid crystal layer over the die. By using such an application, the liquid crystal analysis described herein is enhanced.

According to another example embodiment of the present invention, a flip chip die having a circuit defect is analyzed. The die has circuitry including the defect in a circuit side opposite a backside, and a liquid crystal layer formed over a thinned region in the back side. A microscope having a polarized light source, an analyzer, and a camera is arranged over the back side. An electrical power source is used to power the die, and the defective circuitry generates heat in response. The power source may, for example, be operated in a continuous loop that includes operational conditions that induce a circuit failure in the die. The generated heat expands radially and heats other portions of the die including the liquid crystal. As the liquid crystal reaches its transition temperature, it changes phase. The phase change is detectable as a dark area when viewed with the microscope. This defect-driven phase change is recorded using the microscope and the camera and used to determine the location of the defect.

The type of liquid crystal used can be selected based upon the type of analysis that is to be performed. For example types of liquid crystal material suitable for use in connection with the present invention, reference may be made to T. W. Lee & S. V. Pabbisetty, *Liquid Crystal Microscopy*, in Microelectronic Failure Analysis 141 (3$^{rd}$ ed., ASM International, 1993). Such liquid crystal is available from various sources and can be chosen to provide a state transition temperature (STT) that is just over room temperature for near-room temperature applications. Other liquid crystal material may be used in applications requiring or benefiting from different properties, such as liquid crystal having a STT that is higher or lower for applications where the testing is done at a different temperature.

According to another example embodiment of the present invention, the power supplied to the internal heat source is varied. For example, effecting the power variation may include altering the frequency of the clock cycle being applied to the die. Higher frequencies operate the die at a faster rate and draw more power. Using a constant voltage source, the resulting current draw increases. Advantages of altering the power include enabling the control of the amount of heat generated by the internal heat source. This is useful for controlling the progression of the liquid crystal phase change. For faster advancement of the leading edge of the phase change, the clock is manipulated to cause the intrinsic heat source to generate more heat. For slower advancement of the leading edge, the clock is manipulated to cause the intrinsic heat source to generate less heat. The rate of heat generation can be controlled by increasing or decreasing the frequency of the clock. The power adjustments may, for example, be performed during the analysis process, or may be preset and held constant throughout the analysis process.

In another example embodiment of the present invention, adjustments are made to keep the leading edge of the phase change due to an intrinsic heat source within the field of view of the microscope. It may also be useful to make adjustments to view different portions of the die, such as when more than one defect is being analyzed. For example, it may be useful to move either the microscope or the die in order to maintain a desired view, particularly when the microscope is focused on a small area of the die. One example manner in which to maintain view of the leading edge of the liquid crystal transition is to mount the die on a moving platform, such as a microscope stage, and move the platform accordingly. Another manner is to move and re-focus the microscope itself on the leading edge of the transition. Still another method is to move both the die and the microscope.

In another example embodiment of the present invention, a cooling arrangement is used to cool the die as it is being analyzed in order to control the intrinsic heating process. For example, the intrinsic heat source may heat the die at such a rate that it is difficult or impossible to sufficiently analyze the die. By cooling the die, the heating rate, and thus the advancement of the leading edge of the transition area, can be slowed or even reversed. Slowing the heating rate helps for defect detection because more time is allowed for obtaining an image of the defect-generated liquid crystal transition before it is engulfed by the leading edge. Reversing the heating rate enables the reversal of the phase transition, allowing the viewing of the defect-generated transition as it transitions back into the original state. One example cooling arrangement includes a filtered compressed gas supply, such as an air supply or a nitrogen supply, adapted to direct the gas at the die.

The cooling arrangement may also be used to speed the analysis process. For example, once the general location of the defect is known, it may be advantageous to heat the die at a fast rate until the leading edge nears the defect. When the defect is neared, the coolant can be used to slow the heat rate and thus slow the expansion of the leading edge as it approaches the defect. Depending upon the die being analyzed, the cooling arrangement can be adjusted to achieve a desired heating rate.

In another example embodiment of the present invention, the heating rate of the die is sufficiently slowed to allow the separate viewing of the phase transitions of the liquid crystal using conventional detection methods, such as using a microscope. This enables liquid crystal-assisted defect detection a die that has more than one defect or an intrinsic heat source located in such proximity to a defect that the heat generated by it overwhelms heat generated at the defect. For instance, when the rate of state change of the liquid crystal is too fast for conventional methods to detect, the power supplied to the die can be altered to reduce the amount of heat supplied, slow the phase change, and allow the viewing of the defect-induced phase change. Similarly, a cooling arrangement such as described hereinabove can be used to cool the die and sufficiently slow the heating (and thus, the state change) of the liquid crystal layer to allow detection of the defect-related state change using conventional methods. In one particular example embodiment, the cooling and heating of the die are controlled in such a manner that the leading edge of the liquid crystal phase transition does not advance. The phase-change advancement is stopped when the defect-related phase transition is present, thereby allowing the static viewing of the defect-generated phase change.

Another manner in which to make the detection of the defect easier is to use a camera to record an image of the liquid crystal phase change as a function of time. The recorded image can, for example, be viewed in slow motion, or viewed in a frame-by-frame mode. Each image (frame) captured by the camera is taken at a sufficiently short time interval that enables the capture of an image of the defect-driven phase change before the leading edge of an intrinsic heat source-driven phase change engulfs the defect. That is, the camera speed must be selected so that each frame is recorded at a time interval that is shorter than the time interval between the occurrence of the defect-driven phase change and the engulfing of the defect-driven phase change by the intrinsic heat-driven phase change.

Figure 2A:
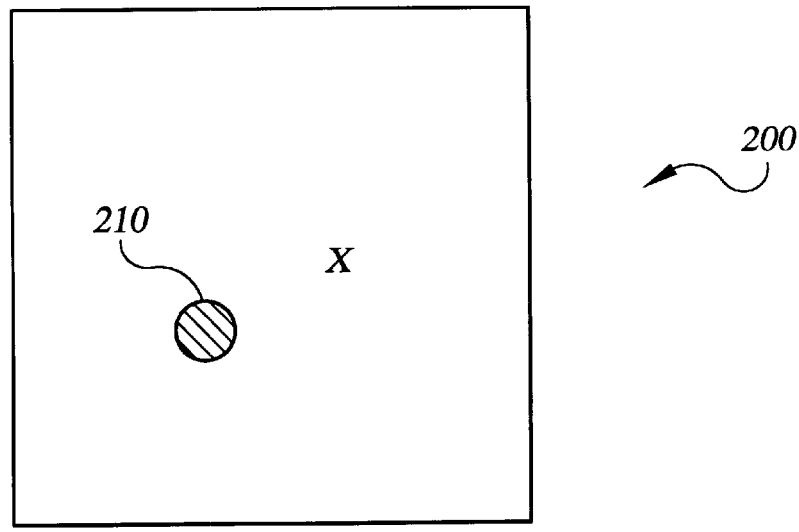
FIG. 2A is a top view of a semiconductor die undergoing analysis, according to another example embodiment of the present invention.
Figure 2B:
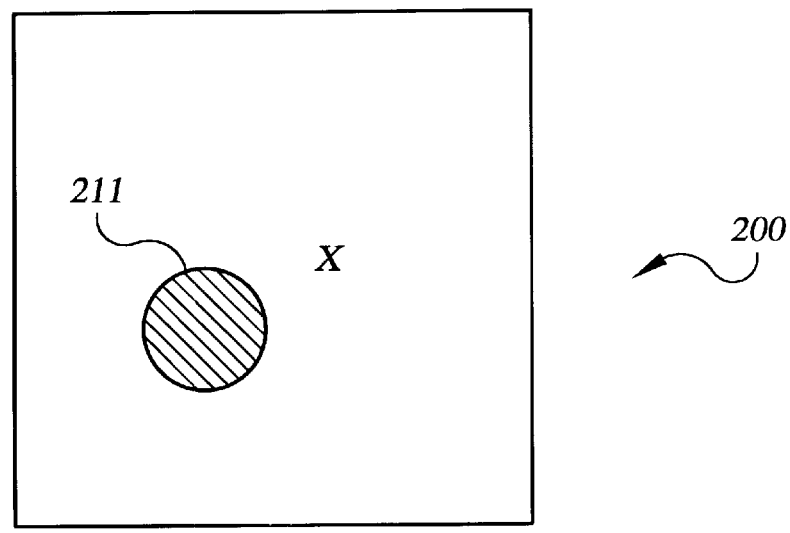
FIG. 2B is a top view of the semiconductor die of FIG. 2A, according to another example embodiment of the present invention.

FIGS. 2A–2D show camera images of a top view of a liquid crystal layer on a semiconductor die 200 changing phase as a result of heat generated in the die, according to another example embodiment of the present invention. The liquid crystal is formed on a thinned region in the back side of the die. The die 200 includes a defect below the liquid crystal layer, shown as X, and an intrinsic heat source. A camera is located over the die and is adapted to capture the time-lapsed images shown. The die is electrically stimulated and the intrinsic heat source generates heat that causes a portion 210 of the liquid crystal layer to change phase, as shown in FIG. 2A. The back side has been thinned sufficiently to facilitate heat transfer to the liquid crystal that allows the location of the defect to be detected while maintaining integrity of the die. As electrical stimulation continues to be applied to the die 200, the portion of the liquid crystal layer that has changed phase expands, shown as portion 211 in FIG. 2B.

Figure 2C:
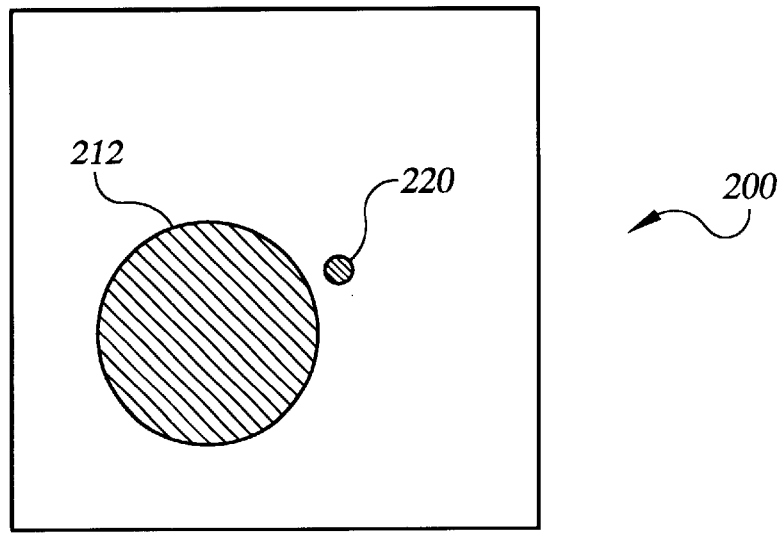
FIG. 2C is a top view of the semiconductor die of FIG. 2A, according to another example embodiment of the present invention.
Figure 2D:
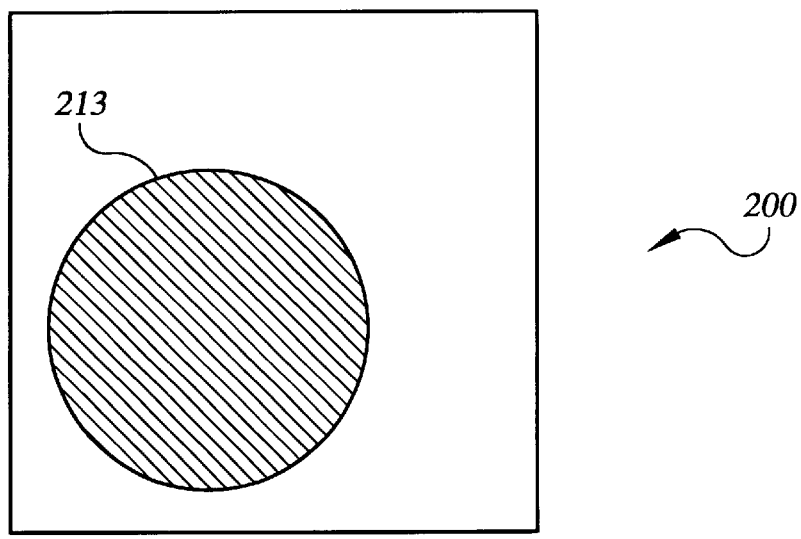
FIG. 2D is a top view of the semiconductor die of FIG. 2A, according to another example embodiment of the present invention.

In addition to the heat generated by the intrinsic heat source, the defect also generates heat. In FIG. 2C, the expanding area of liquid crystal having undergone a phase change 212 has nearly reached the portion of liquid crystal over the defect. At this point, the combined heat generated by the intrinsic heat source and the defect is sufficient to cause a portion 220 of the liquid crystal to change phase. The camera is adapted to capture the image of this phase change before the expanding area engulfs the portion 220, as shown in FIG. 2D.

Referring again to FIGS. 2C and 2D, and according to another example embodiment of the present invention, a cooling arrangement is used to reverse the phase transition, such as described herein above. If the transition to FIG. 2D occurs too fast, the application of a cooling arrangement can be used to reverse the transition so that the phase transition regresses to the image shown in FIG. 2C. In this manner, the defect can be detected even if the advancement of the phase transition is too rapid for analysis without a cooling arrangement. In addition, the power supply to the die can also be adjusted to control the amount of heat generated in the die and to enable the regression of the liquid crystal phase change from FIG. 2D to FIG. 2C. The power adjustment can be used alone or in conjunction with the cooling arrangement to achieve the desired result.

Figure 3:
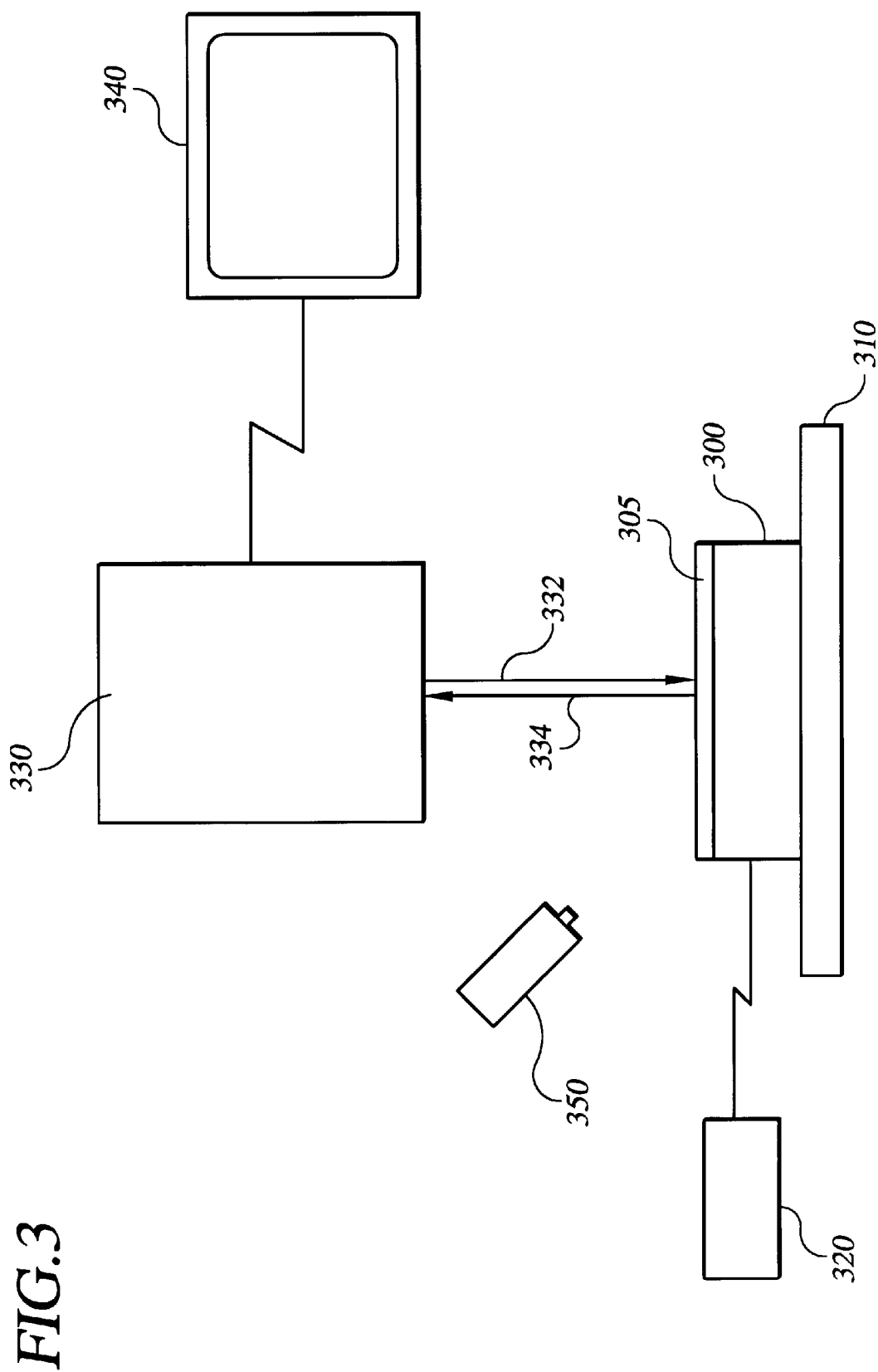
FIG. 3 is a system for analyzing a semiconductor die, according to another example embodiment of the present invention.

FIG. 3 is a system adapted to detect a defect using a liquid crystal phase change, according to another example embodiment of the present invention. The system may, for example, be used to create the images shown in FIGS. 2A–2D. The system includes a movable stage 310 adapted to hold a flip chip die 300 having a liquid crystal layer 305 formed over a thinned region in a back side of the die. A power supply 320 is coupled and adapted to supply power to the die and to generate heat in circuitry in the die. A detection arrangement 330 is arranged over the liquid crystal layer 305 and is adapted to capture an image of the liquid crystal as it changes phase due the heat generated. The captured image may, for example, be one of several images captured over time, such as by a camera or a video camera. A polarized light source is adapted to direct polarized light 332 at the die 300. An analyzer (linear polarizer) is arranged so that an image 334 from the die 300 passes through it before it is captured. In one particular implementation, the detection arrangement 330 includes a laser scanning microscope having a polarized laser source adapted to create a laser beam having a wavelength of about 1064 nanometers, and an analyzer.

The heat may, for example, be generated by a defect and/or by an intrinsic heat source. In the instance where heat is generated by a defect, the detection arrangement 330 is adapted to capture an image of the liquid crystal changing phase, and the image can be used to locate the defect. In the instance where an intrinsic heat source is located near a defect, the system 300 is adapted to distinguish the defect-related phase change from that related to the intrinsic heat source. The defect-related phase change occurs momentarily before the phase change generated by the intrinsic heat source in the die, such as discussed hereinabove. The detection arrangement 330 is adapted to capture the image before the defect-related phase change ceases to be separately viewable from the phase change caused by the intrinsic heat source.

The detection arrangement optionally includes a monitoring arrangement 340 adapted to display an image of the phase change of the liquid crystal layer 305. In one implementation, the monitoring arrangement includes a video recorder adapted to receive the image data captured by the detection arrangement 330. The video recorder can be used to display the image data in slow motion or frame-by-frame mode to facilitate the viewing of the defect-generated phase change.

In another example embodiment, the power supply 320 is further adapted to modulate the amount of heat generated in the die. For example, altering the clock frequency as described hereinabove causes the die to speed up, draw more power and generate more heat. The altered clock cycle alters the amount of heat generated in the die, and can be chosen to correspond with the type of intrinsic heat source that is in the die.

In another instance, the system further includes a cooling arrangement 350. The cooling arrangement is adapted to cool the die and to control the advancement of the phase change of the liquid crystal layer. For example, the cooling arrangement can be used to supply a gas, such as compressed air or nitrogen. A filter (not shown) is adapted to remove particulates from the gas, and may be included in the filter arrangement or be located externally to the cooling arrangement. The cooling arrangement may be used alone or in conjunction with altering the power supply to the die for controlling the advancement of the liquid crystal phase change.

In another example embodiment, the test arrangement includes image storage and overlay capabilities including for example, emission microscopy for imaging, and RGB for overlaying. One example device that may be included in the test arrangement for emission microscopy is a laser scanning microscope having a wavelength of about 1064 nanometers. The image of circuitry in the die being tested can be stored before performing the liquid crystal analysis. The test arrangement used the image of the phase change and overlays that image onto the image of the circuitry. In one implementation, the test arrangement is adapted to capture an image of the phase change directly. In another implementation, the test arrangement is adapted to mark the phase change with a graphic marker. The stored image data may also be from another die, such as a non-defective reference having similar structure to the die being analyzed. For using a reference die, the system 300 is adapted to first capture an image of the circuitry in the reference die, and then proceed with analysis of the die being tested.

In another example embodiment, the power supply 320 is further adapted to modulate the amount of heat generated in the die by responding to a modulation of the clock frequency. Higher frequencies alter the amount of heat generated in the die, and can be chosen to correspond with the type of defect or intrinsic heat source that is in the die. For instance, by reducing the frequency of the clock, the die slows down and less power is drawn, resulting in less heating in the die.

In another instance, the system further includes a cooling arrangement 350. The cooling arrangement is adapted to cool the die and to control the advancement of the phase change of the liquid crystal layer. For example, the cooling arrangement can be used to supply a gas, such as compressed air or nitrogen. A filter (not shown) is adapted to remove particulates from the gas, and may be included in the filter arrangement or be located externally to the cooling arrangement. The cooling arrangement may be used alone or in conjunction with altering the power supply to the die for controlling the advancement of the liquid crystal phase change.

In another example embodiment, the system of FIG. 3 includes a substrate removal device and a liquid crystal deposition device (not shown) and may, for example, include devices such as a laser etching device or a chemical-mechanical polishing (CMP) device. The substrate removal device is adapted to remove substrate from the chip 300 and form a thinned region in a back side of the chip. The substrate removal device is adapted to polish the thinned region such that any scratches are less than about 3 microns in depth, and that liquid crystal will adhere to the thinned region. The liquid crystal deposition device is adapted to form the liquid crystal layer 305 and may include, for example, a syringe adapted to drop liquid crystal mixed with a solvent onto the thinned region. The solvent evaporates, leaving the liquid crystal behind.

Figure 4:
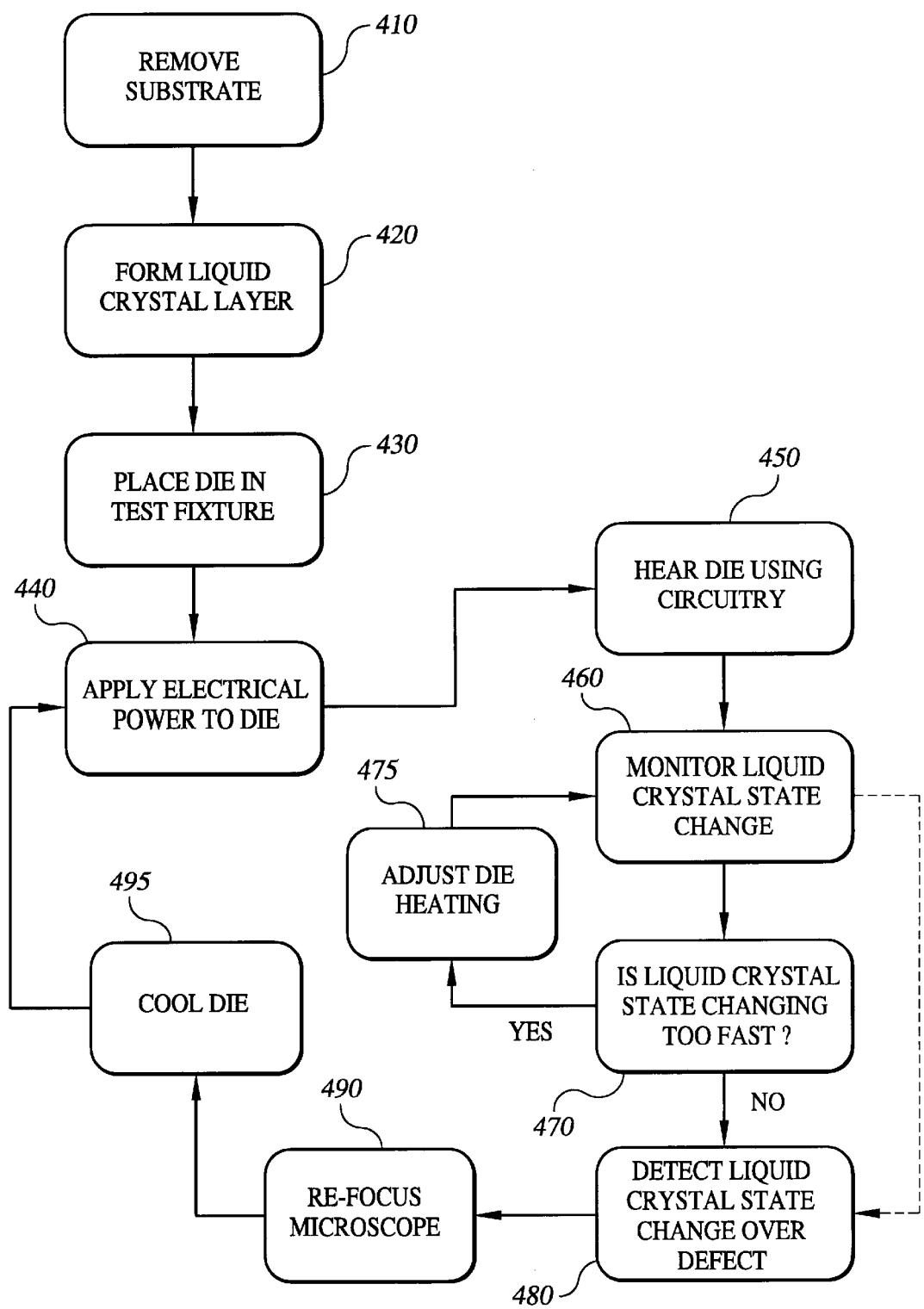
FIG. 4 is a flow diagram of a method for using the system of FIG. 3 for analyzing a semiconductor die, according to an example embodiment of the present invention.

FIG. 4 is a flow diagram of a method for analyzing a flip chip die having a defect using a system, such as the system in FIG. 3, according to another example embodiment of the present invention. A substrate removal device is used to remove a portion of substrate from a back side of the die at block 410. The die includes a defect in the circuit, and may also include an intrinsic heat source. After the portion of substrate has been removed, a liquid crystal layer is formed on a region thinned by the substrate removal at block 420. For example, adding a solvent such as pentane to liquid crystal and using a deposition arrangement, such as a syringe, to deposit the liquid crystal on the die will form a sufficient liquid crystal layer. A liquid crystal emulsion can also be used and applied using an air blast, such as described hereinabove. Other solvents and/or various types of liquid crystal may also be used.

After the liquid crystal layer is formed, the die is placed in a test fixture at block 430, and is powered at block 440. In response to the supplied power, circuitry in the die generates heat at block 450. At block 460, the liquid crystal layer is monitored for a state change in response to the generated heat. In the instance where the defect-generated phase change does not require time-lapsed analysis (e.g., any intrinsic heat sources do not overwhelm heat generated by the defect), after block 460, the process proceeds to block 480, where the defect is detected.

In the instance where the die includes an intrinsic heat source that overwhelms the heat generated by the defect, time-lapsed analysis may be useful for locating the defect. If the liquid crystal state is changing too fast at block 470, the die heating is adjusted at block 475. The adjustment may include, for example, altering the power supply or using a cooling device to cool the die. Once the adjustment is made, the process continues at block 460. If the liquid crystal state is not changing too fast at block 470, a liquid crystal state change is detected at block 480. The state change detected is due at least in part to heat generated at a defect in the device, and is detected as a state change that occurs momentarily before the state change being driven by the intrinsic heat source. The detection may include, for example, capturing video images of the state change at an image capture interval sufficiently short to enable the viewing of the defect-generated state change prior to it being engulfed by the intrinsic heat source-driven state change.

In another alternate example embodiment using a microscope to monitor the liquid crystal state change, the microscope is re-focused at block 490 after the state change is detected at block 480. After the microscope is refocused, the die is allowed to cool sufficiently at block 495 so that the liquid crystal changes back to its original state prior to being heated, and the process continues at block 440. In this manner, the location of the defect can be generally detected, and then subsequently more specifically located using the refocused microscope.

In another example embodiment of the present invention, after the liquid crystal state change is detected at block 480, the microscope is focused on the defect so that the position of the defect in a viewed image through the microscope is easily determined. The die being analyzed is then removed from the test fixture. While maintaining the microscope in the same position and focus, another die having similar structure to the die being analyzed and having a portion of the circuitry exposed is placed in the test fixture. The exposed circuitry can then be viewed and, using the known position of the defect in the viewed image, the portion of circuitry having a defect is determined.

In still another example embodiment, discovered in connection with the present invention, a laser-scanning microscope (LSM) can be used to peer through the liquid crystal layer and image the circuitry. By forming the liquid crystal layer at a distance of about 80 microns or less over the circuitry, the image of the defective circuitry can be obtained with the die being analyzed. When the liquid crystal layer is formed at a distance of about 5–10 microns over the circuitry, other commonly-available microscopes can be used to image the circuitry. Accordingly, using this example embodiment in connection with FIG. 4, after the liquid crystal state change has been detected at block 480, the circuitry below the liquid crystal layer is imaged. In this manner, the particular circuitry below the defect-generated phase change can be detected.

While the present invention has been described with reference to several particular example embodiments, those skilled in the art will recognize that many changes may be made thereto without departing from the spirit and scope of the present invention, which is set forth in the following claims.

What is claimed is:

1. A method for analyzing a flip chip die, the method comprising:

providing a flip chip die having a back side opposite circuitry at a circuit side and having a liquid crystal layer formed over a thinned region in the back side;

generating heat in the die circuitry; and detecting a defect in the die by detecting a portion of the liquid crystal changing phase.

2. The method of claim 1, wherein providing a flip chip die having a liquid crystal formed over a thinned region in the back side comprises:

removing at least a portion of a substrate from the back side and forming the thinned region; and forming a liquid crystal over at least a portion of the thinned region.

3. The method of claim 2, wherein removing at least a portion of the substrate from the back side and forming the thinned region includes removing an amount of the substrate sufficient to allow heat transfer for the liquid crystal analysis while not allowing the die to be damaged during removal from a package.

4. The method of claim 2, wherein removing at least a portion of the substrate from the back side and forming the thinned region includes forming a thinned region having sufficient roughness to facilitate the formation of the liquid crystal.

5. The method of claim 2, wherein forming the liquid crystal includes at least one of: mixing liquid crystal material with a solvent sufficient to allow the liquid crystal to flow, wherein the solvent evaporates and leaves the liquid crystal behind; and depositing a liquid crystal emulsion on the thinned region and directing an air blast to the emulsion.

6. The method of claim 1, wherein generating heat in the die circuitry includes heating the die using an external heat source.

7. The method of claim 1, wherein generating heat in the die circuitry includes coupling a power source to the die and electrically operating the die.

8. The method of claim 7, further comprising varying the output of the power source to change the heating rate of the circuitry within the die.

9. The method of claim 7, wherein electrically operating the die includes operating the die in a continuous loop that includes operational conditions that induce a circuit failure.

10. The method of claim 1, wherein detecting a defect in the die includes using a laser scanning microscope having a polarized light source and an analyzer.

11. The method of claim 1, wherein the testing arrangement includes a microscope, further comprising:

obtaining a reference image of circuitry;

using the microscope to obtain an image of the defect-related liquid crystal phase change in the die; and superimposing the defect-related image over the reference image and providing a visual representation of the portion of circuitry having a defect.

12. The method of claim 11, wherein the reference image is of the circuitry in a non-defective reference die having structure about identical to the die.

13. The method of claim 11, wherein the reference image is of the circuitry in the die.

14. The method of claim 11, wherein using the microscope to obtain an image of the defect-related liquid crystal phase change in the die includes at least one of photographing the phase change and marking the phase change with a graphic marker.

15. The method of claim 11, further comprising using the superimposed defect image over the reference image to distinguish a liquid crystal phase change due to intrinsic heat sources from a liquid crystal phase change due to a defect.

16. The method of claim 7, wherein electrically operating the die comprises electrically operating a first circuit region and causing the first circuit region and a second circuit region having a defect to effect a separately viewable phase change in corresponding areas of the liquid crystal, the first and second circuit regions being selected to cause the corresponding phase changes to cease to be separately viewable by conventional real-time analysis.

17. The method of claim 16, wherein detecting a defect in the die as a portion of the liquid crystal changing phase comprises detecting the liquid crystal phase change in the area corresponding to the second circuit region before the corresponding areas cease to be separately viewable.

18. The method of claim 1, further comprising cooling the die.

19. The method of claim 18, wherein cooling the die includes terminating the heat generation in the die, further comprising re-generating heat in the die circuitry and re-detecting the defect in the die after the die has cooled.

20. The method of claim 18, wherein cooling the die includes directing a cooling agent at the die, the cooling agent comprising at least one of: compressed air and compressed nitrogen.

21. A system for analyzing a flip chip die having a back side opposite circuitry at a circuit side and a liquid crystal, the system comprising:

means for providing a flip chip die having the liquid crystal formed over a thinned region in the back side;

means for generating heat in the die circuitry; and means for testing the die, the testing means adapted to detect a defect as a portion of liquid crystal changing phase.

22. A system for analyzing a flip chip die, the flip chip die having a back side opposite circuitry at a circuit side and a liquid crystal, the system comprising:

an arrangement adapted to provide a flip chip die having the liquid crystal formed over a thinned region in the back side;

an heat generation arrangement adapted to generate heat in the die circuitry; and a testing arrangement adapted to detect a defect in the die as a portion of the liquid crystal changing phase.

23. The system of claim 22, wherein the arrangement adapted to provide a flip chip die having a liquid crystal formed over a thinned region in the back side comprises:

a substrate removal device adapted to remove substrate from the back side of the flip chip die and form a thinned region; and a deposition arrangement adapted to form a liquid crystal on the thinned region.

24. The system of claim 23, wherein the substrate removal device is further adapted to form a thinned region having sufficient surface qualities to adhere to the liquid crystal.

25. The system of claim 22, wherein the testing arrangement includes a microscope having a polarized light source and an analyzer.

26. The system of claim 25, wherein the microscope includes a laser scanning microscope.

27. The system of claim 26, wherein the laser scanning microscope is adapted to use emission microscopy to obtain an image of the die and to use an RGB function to superimpose the test image onto a reference image.

28. The system of claim 27, wherein the laser scanning microscope is adapted to produce a laser beam having a wavelength of about 1064 nanometers.

29. The system of claim 25, wherein the microscope includes a stage adapted to hold the die.

30. The system of claim 29, wherein the stage is adapted to move and to keep a selected portion of the die within the field of view of the microscope.

31. The system of claim 25, wherein the testing arrangement is adapted to record an image of the die as a function of time, the image being indicative of the liquid crystal changing phase.

32. The system of claim 31, wherein the testing arrangement includes a storage arrangement adapted to store image data.

33. The system of claim 32, wherein the storage arrangement is adapted to play back image data in slow motion.

34. The system of claim 31, wherein the testing arrangement includes a camera.

35. The system of claim 22, wherein the heat generation arrangement includes a power supply adapted to electrically operate the die.

36. The system of claim 35, wherein the power supply is adapted to respond to variations in a clock frequency supplied to the chip.

* * * * *